United States Patent [19]

Farbood et al.

[11] Patent Number: 4,560,656

[45] Date of Patent: Dec. 24, 1985

[54] PRODUCTION OF γ-DECALACTONE

[75] Inventors: Mohamad I. Farbood, Princeton; Brian J. Willis, Ramsey, both of N.J.

[73] Assignee: Fritzsche Dodge & Olcott Inc., New York, N.Y.

[21] Appl. No.: 448,891

[22] PCT Filed: Sep. 27, 1982

[86] PCT No.: PCT/US82/01323

§ 371 Date: Dec. 1, 1982

§ 102(e) Date: Dec. 1, 1982

[87] PCT Pub. No.: WO83/01072

PCT Pub. Date: Mar. 31, 1983

[51] Int. Cl.$^4$ ............... C12P 7/26; C12P 7/02; C12P 7/00; C12P 7/64; C12P 7/42; C12N 9/14; C12N 1/20; C07B 19/02

[52] U.S. Cl. ............... 435/146; 435/132; 435/134; 435/136; 435/148; 435/155; 435/195; 435/198; 435/280

[58] Field of Search ............... 435/132, 134, 136, 146, 435/148, 155, 195, 198, 253, 254, 255, 271, 280, 822, 911, 923

[56] References Cited

U.S. PATENT DOCUMENTS

| | | | |
|---|---|---|---|
| 3,076,750 | 2/1963 | Muys et al. | 435/136 |
| 3,562,112 | 2/1971 | Gibian et al. | 435/136 |
| 4,059,488 | 11/1977 | Hachikubo et al. | 435/134 |
| 4,204,044 | 5/1980 | Suhara et al. | 435/280 |
| 4,275,081 | 6/1981 | Coleman et al. | 435/134 |
| 4,302,540 | 11/1981 | Hirata et al. | 435/280 |

FOREIGN PATENT DOCUMENTS 0170193 10/1982 Japan ............... 435/134

OTHER PUBLICATIONS

Okui, S. et al., *The Journal of Biochemistry*, vol. 54, No. 6, pp. 536–540, (1963), "Metabolism of Hydroxy Fatty Acids".

Final, I. L. *Organic Chemistry*, vol. 1, 6th Edition, Longman Group Limited, London, pp. 468–472, (1973).

Okui et al., Biochim. Biophys. Acta, 70, (1963), pp. 346–348.

*Primary Examiner*—Thomas G. Wiseman
*Assistant Examiner*—Robin Teskin
*Attorney, Agent, or Firm*—Cooper, Dunham, Clark, Griffin & Moran

[57] ABSTRACT

Optically active γ-decalactone is produced by culturing a microorganism capable of hydrolyzing castor oil and effecting β-oxidation of the resulting hydrolysate in the presence of castor oil or castor oil hydrolysate and a co-oxidant. The resulting γ-hydroxydecanoic acid is lactonized to form γ-decalactone.

4 Claims, No Drawings

PRODUCTION OF γ-DECALACTONE

BACKGROUND OF THE INVENTION

This invention is concerned with a microbial process for the production of optically active γ-decalactone. Considerable time and effort have been expended by microbiologists in the search for better processes for the production of optically active lactones. U.S. Pat. No. 3,076,750 disclose a method of preparing certain optically active lactones and the corresponding hydroxycarboxylic acids by microbial reduction of ketocarboxylic acids. The metabolism of ricinoleic acid by some Candida strains was investigated by Okui et al. (J. Biochemistry, 54,536–540, 1963) who showed that γ-hydroxydecanoic acid was an intermediate in the oxidative degradation of ricinoleic acid. However, only trace amounts of γ-hydroxydecanoic acid were recovered from the fermentation medium due to the metabolysis of γ-hydroxydecanoic acid upon completion of the fermentation, and the toxicity of ricinoleic acid to the microorganism, which limits the amount of substrate that can be used.

SUMMARY OF THE INVENTION

This invention provides a method of producing optically active γ-hydroxydecanoic acid which coprises culturing or incubating a microorganism capable of hydrolyzing castor oil, and effecting β-oxidation of the resulting hydrolysate in the presence of castor oil, to produce γ-hydroxydecanoic acid.

In another embodiment, the invention provides a method of producing optically active γ-hydroxydecanoic acid which comprises enzymatically hydrolyzing castor oil using lipase to form an enzymatic hydrolysate and culturing or incubating a microorganism capable of effecting β-oxidation of the enzymatic hydrolysate in the presence of said hydrolysate to produce γ-hydroxydecanoic acid.

In still another embodiment, the invention provides a method of producing optically active γ-hydroxydecanoic acid which comprises culturing or incubating a microorganism capable of hydrolyzing castor oil and a microorganism capable of effecting β-oxidation of castor oil hydrolysate in the presence of castor oil to produce γ-hydroxydecanoic acid.

DETAILED DESCRIPTION OF THE INVENTION

The invention provides a fermentation process for the production of optically active γ-hydroxydecanoic acid which may optionally be converted by lactonization to γ-decalactone. Depending on the embodiment of the invention employed, the fermentation process involves culturing or incubating a microorganism capable of hydrolyzing castor oil and effecting β-oxidation of the resulting hydrolysate, or a microorganism capable of effecting β-oxidation of hydrolysate of castor oil, or a microorganism capable of effecting β-oxidation of an enzymatic hydrolysate of castor oil, in a suitable medium in the presence of the castor oil or castor oil hydrolysate substrate. The use of castor oil or castor oil hydrolysate as the substrate is determined by the microorganism(s) employed in the process. A co-oxidant may be added to the culture medium in order to increase the yield of the process.

The selection of the appropriate microorganism for the process is crucial depending on the embodiment of the invention employed, the yield of product required, and the resistance to the toxicity of the fatty acids found in the castor oil hydrolysate. The microorganisms in the invention may be bacteria, yeast or filamentous fungi. Where a microorganism is employed to hydrolyze the castor oil substrate and β-oxidize the resulting hydrolysate, the preferred microorganisms are: *Aspergillus oryzae, Candida rugosa, Geotrichum klebahnii* or *Yarrowia lipolytica*, (formerly known as *Saccharomycopsis lipolytica* and previously *Candida lipolytica*), more preferably *Yarrowia lipolytica*. Where the microorganism is employed to only β-oxidize castor oil hydrolysate, the preferred microorganisms are: *Hansenula saturnus, Candida guilliermondii, Candida albicans, Candida krusei, Candida parakrusei, Candida pseudotropicals, Candida stellatoidea, Candida tropicalis, Aspergillus oryzae, Candida rugosa, Geotrichum klebahnii* or *Yarrowia lipolytica*, more preferably *Candida guilliermondii*. Where the microorganism is used in combination with a lipase and with castor oil, the preferred microorganisms are: *Hansenula saturnus, Candida guilliermondii, Candida albicans, Candida krusei, Candida parakrusei, Candida pseudotropicalis, Candida stellatoidea, Candida tropicalis, Aspergillus oryzae, Candida rugosa, Geotrichum klebahnii* or *Yarrowia lipolytica*, more preferably *Candida guilliermondii*. Generally, any type of lipase enzyme may be used to hydrolyze the castor oil, including microbial, pancreatic, fungi or yeast.

Where a lipase is used with the microorganism in the process of the invention, the formation of the enzymatic hydrolysate may be controlled by limiting the amount of lipase used in the process. This will avoid toxicity resulting from the presence of excessive amounts of hydrolysate. The appropriate amount of lipase required may be conveniently found by experimentation and will depend upon the lipase and microorganism used and the culturing conditions. The hydrolysis using lipase is most preferably carried out concurrently with the fermentation in the same reaction vessel. However, the hydrolysis may be carried out prior to fermentation if appropriate measures are taken to avoid the toxic effect of the hydrolysate. When castor oil is used in the invention, the concern for toxicity is eliminated because triglycerides are not toxic to the organisms. Additionally, the use of castor oil and castor oil hydrolysates as the substrate provide co-oxidants to the process which increase efficiency due to the presence of other fatty acids upon hydrolysis of the castor oil.

The form in which the microorganisms are used is not critical. They can be used as the culture (suspension), i.e., including the cells and the corresponding nutrient solution, or in the form of cells suspended in a buffer solution. The cells or an enzyme extract thereof may be immobilized on a suitable solid support which may then be used to effect the transformations.

The culture suspension is prepared by inoculation of a suitable medium with the microorganism. A suitable medium is one which contains carbon sources, nitrogen sources, inorganic salts and growth factors. Among the suitable carbon sources are for example, glucose, galactose, L-sorbose, maltose, sucrose, cellobiose, trehalose, L-arabinose, L-rhamnose, ethanol, glycerol, L-erythritol, D-mannitol, lactose, melibiose, raffinose, meleritose, starch, D-xylose, D-sorbitol, α-methyl-D-glucoside, lactic acid, citric acid and succinic acid. Among the suitable nitrogen sources are, for example, nitrogen-containing organic substances such as peptone, meat extract, yeast extract, corn steep liquor, and casein, urea, amino acids, or nitrogen containing inorganic compounds such as nitrates, nitriles, and inorganic ammonium salts. Among the suitable inorganic salts are, for example, phosphates, magnesium, potassium, calcium, sodium. The above mentioned nutrients in the culture medium may be supplemented with, for example, one or more vitamins of the B Group and/or one or more trace minerals such as Fe, Mo, Cu, Mn, B as desired. However, the process can be performed in a vitamin-free medium, for example, when a small amount of yeast extract is added to the medium there is no need for vitamins or trace minerals.

The cultivation of the microorganism can be carried out as a stationary culture or as a submersed culture (e.g., shaking culture, fermentors) preferably under aerobic conditions. One suitably may work in the pH range of from about 3.5 to about 8.0, and preferably in the range of from about 4.0 to about 7.5. The pH may be regulated by the addition of inorganic or organic bases, such as sodium hydroxide, potassium hydroxide, calcium hydroxide, calcium carbonate, by ion-exchange resins, or by the addition of a buffer such as phosphate or phthalate. The incubation temperature is suitably maintained at between about 15° C. and about 33° C., with a range from about 20° C. to about 30° C. being preferred.

The process in accordance with the invention is conveniently carried out by adding castor oil or castor oil hydrolysate, as the substrate, to the culture medium at the onset of cultivation, as the sole carbon source. Alternatively, the substrate may be added in combination with another carbon source, such as dextrose, either during cultivation, or when cultivation is complete. The amount, level, or concentration of the substrate in the medium may vary. For example, in the case of hydrolyzed castor oil, levels of from about 0.3% to about 5% may make up the medium initially or be added during the course of the fermentation, whereas substantially any level of castor oil may be used.

The reaction time may vary depending on the composition of the culture medium and the substrate concentration. In general, shaking flask cultures require from between about 2 h. and about 240 h. depending upon the microorganism and the composition of the culture medium. However, when a fermentor is used the fermentation time may be reduced to about 100 h. or less.

The fermentation may be carried out using the cells of the microorganism isolated from the culture solution, or with an enzyme extract isolated from the cells in a manner known per se. In this case, the fermentation can be conveniently carried out in aqueous solution, for example in a buffer solution, in a physiological salt solution, in a fresh nutrient solution, or in water. The isolated cells or enzyme extract may be immobilized on a solid support and the desired transformation effected in the absence of the live microorganism. The transformation of the substrate may be effected by mutants of the microorganism. Such mutants can be obtained readily by methods well known in the art, for example, by exposing the cells to UV or X-rays, or customary mutagenic substances such as for example, acridine orange.

The substrate is generally added directly to the medium. A surface-active agent or dispersion agent, such as Tween 80 (polyoxyethylenesorbitan monostearate), can also be added to an aqueous suspension of the substrate. Conventional antifoam agents, such as silicone oils (e.g., UCON), polyalkyleneglycol derivatives, maize oil, or soya oil can be used to control foaming.

The transformation of the substrate can be monitored using standard analytical techniques such as GLC, TLC, HPLC, IR and NMR. If a rapid disappearance of the substrate is observed, more substrate can then be added in order to maximize the transformation capacity of the microorganisms. The incubation is generally terminated when all the substrate has disappeared from the culture medium.

After the fermentation process is complete, the γ-hydroxydecanoic acid can either be lactonized in the medium to form γ-decalactone, or isolated and purified by conventional techniques including solvent extraction and distillation. When in situ lactonization is desired, the pH of the medium is adjusted to between about 1 and about 5, preferably between about 1 and about 3, by the addition of a suitable acid, such as hydrochloric acid, and the resulting mixture heated to between about 50° C. and about 100° C., preferably between about 70° C. and about 100° C. for about ten minutes, depending upon the temperature, to convert the γ-hydroxydecanoic acid to γ-decalactone. The γ-decalactone is then recovered and purified by standard techniques. If the γ-hydroxydecanoic acid is recovered, it may be lactonized according to known procedures [see, for example, I. L. Finar, Organic Chemistry, 6th ed., Vol. 1, p 469 (1973)].

The following examples serve to illustrate embodiments of the invention as it is now preferred to practice it but in no way are meant to limit the scope thereof. Unless otherwise stated, weights are in grams, temperatures are in degrees centigrade and pressure in mm Hg.

EXAMPLE I

A flask containing 100 ml of 2% beef extract and 0.02% Tween 80 was autoclaved at 120° C. for 20 minutes. The medium was then inoculated with $10^7$ cells Yarrowia lipolytica (Saccharomycopsis lipolytica)/ml of medium, and 10 g of castor oil added. The culture was incubated at 26° C. on a rotary shaker (200 rpm) for one week. The pH of the medium was occasionally adjusted to 6.5–7.0. At the end of the fermentation period the pH of the medium was adjusted to 1.5 by the addition of mineral acid, and the mixture heated at 100° C. for 10 minutes. After cooling, the organic products were extracted with hexane, and hexane evaporated, and the residue distilled to provide 0.61 g γ-decalactone having a GLC purity of 90%.

EXAMPLE II

The procedures and materials similar to those described in Example I were followed, except 0.05 g decanoic acid was added each day. There was obtained 0.69 g γ-declactone having a GLC purity of 92%.

EXAMPLE III

The procedures and materials similar to those described in Example I, except that Candida guilliermondii was used and 3 g were followed of castor oil hydrolysate was added. There was obtained the desired product γ-decalactone in 34% yield.

EXAMPLE IV

By employing the procedures and materials similar to those described in Example I except that lipase is added in conjunction with castor oil, there may be obtained the desired product, γ-decalactone.

EXAMPLE V

By employing the procedures and materials similar to those described in Examples I, II and III except that other members of the genus Candida such as *C. albicans, C. krusei, C. parakrusei, C. pseudotropicalis, C. stellatoidea, C. tropicalis,* etc., are used, there may be obtained the desired γ-decalactone.

EXAMPLE VI

By employing the procedures and materials similar to those described in Example I, except that as a microorganism *Aspergillus oryzae* is used and 3 g of castor oil is added, there is obtained the desired product γ-decalactone (0.86 g/L).

EXAMPLE VII

By employing the procedures and materials similar to those described in Example I, except that as a microorganism *Geotrichum klebahnii* is used and 3 g of castor oil is added, there is obtained the desired product γ-decalactone (0.2 g/L).

EXAMPLE VIII

By employing the procedures and materials similar to those described in Example I, except that as a microorganism *Candida guilliermondii* is used and to each 100 ml of medium 100 mg of a lipase (steapsin, Nutritional Biochem Corp.) is added, the desired product γ-decalactone may be obtained.

The invention being thus described, it will be obvious that the same may be varied in many ways. Such variations are not to be regarded as a departure from the spirit and scope of the invention and all such modifications are intended to be included within the scope of the following claims:

What is claimed is:

1. A method of producing gama-decalactone comprising culturing fungi selected fro the group consisting of *Aspergillus oryzae, Geotrichum klebahnii* and *Yarrowia lipolytica* which hydrolyze and beta-oxidize castor oil in a medium comprising castor oil, said culturing taking place at a pH of about 3.5 to about 8.0, at a temperatur 15°–33° C. and for a period of time in the range from about 2 to about 240 hours so as to produce optically active gamma-hydroxydecanoic acid, thereupon in situ lactonizing the resulting produced gamma-hydroxydecanoic acid at a pH of from about 1 to about 5 and at a temperature in the range from about 50° C. for a sufficient period to convert the gamma-hydroxydecanoic acid to gamma-decalactone and recovering the resulting prodcued gamma-decalactone.

2. A method of producing gamma-decalactone which comprises culturing fungi selected from the group consisting of *Aspergillus oryzae, Geotrichum klebahnii, Yarrowia lipolytica* and *Hansenula saturnus* which beta-oxidize castor oil hydrolysate in a medium comprising castor oil hydrolysate, said culturing being carried out at a pH of from about 3.5 to about 8.0, at a temperature in the range from about 15° C. to about 33° C. and for a period of time from about 2 to about 240 hours to produce gamma-hydroxydecanoic acid, subjecting the produced gamma-hydroxydecanoic acid to in situ lactonization at a pH in the range from about 1 to about 5, at a temperature in the range from about 50° C. to about 100° C. and for a period of time sufficient to convert in situ the gamma-hydroxydecanoic acid to gamma-declactone and recovering the resulting produced gamma-declactone.

3. A method of producing gamma-decalactone comprising enzymatically hydrolyzing castor oil by employing lipase to form an enzymatic hydrsolysate, culturing fungi selected from the group consisting of *Aspergillus oryzae, Geotrichum klebahnii, Yarrowia lipolytica* and *Hansenula saturnus* which beta-oxidize said enzymatic hydrolysate in a medium comprising said hydrolysate, said culturing operation taking place at a pH in the range from about 3.5 to about 8.0 at a temperature in the range from about 15° C. to about 33° C. and for a period of time in the range from about 2 hours to about 240 hours to produce gamma-hydroxydecanoic acid, thereupon in situ lactonizing the resulting gamma-hydroxydecanoic acid to gamma-decalactone, said in situ lactonization operation being carried out at a pH in the range from about 1 to about 5, at a temperature in the range from about 50° C. to about 100° C. and for a period of time sufficient to convert said gamma-hydroxydecanoic acid to gamma-decalactone and recovering the resulting produce gamma-declactone.

4. A method of producing gamma-decalactone which comprises culturing the fungus *Yarrowia lipolytica* in a medium comprising castor oil at a pH in the range from about 3.5 to about 8.0, at a temperature in the range from about 15° C. to about 33° C. and for a period of time in the range from about 2 hours to about 240 hours to produce gamma-hydroxydecanoic acid, thereupon in situ lactonizing the resulting produced gammahydroxydecanoic acid at a pH in the range from about 1 to about 5 at a temperature in the range from about 50° C. to about 100° C. for a period of time sufficient to convert the gamma-hdyroxydecanoic acid to gamma-decalactone and recovering the resulting produced gamma-decalactone.

* * * * *